(12) United States Patent
Steger (10) Patent No.: US 11,980,504 B2
(45) Date of Patent: May 14, 2024

(54) FIBER BRAGG GRATING END EFFECTOR FORCE SENSOR

(71) Applicant: Intuitive Surgical Operations, Inc., Sunnyvale, CA (US)

(72) Inventor: John Ryan Steger, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 842 days.

(21) Appl. No.: 17/058,630

(22) PCT Filed: May 24, 2019

(86) PCT No.: PCT/US2019/033986
§ 371 (c)(1),
(2) Date: Nov. 24, 2020

(87) PCT Pub. No.: WO2019/227032
PCT Pub. Date: Nov. 28, 2019

(65) Prior Publication Data
US 2021/0205043 A1  Jul. 8, 2021

Related U.S. Application Data

(60) Provisional application No. 62/676,653, filed on May 25, 2018.

(51) Int. Cl.
*A61B 90/00* (2016.01)
*A61B 34/35* (2016.01)
*G01L 1/24* (2006.01)

(52) U.S. Cl.
CPC .............. *A61B 90/06* (2016.02); *A61B 34/35* (2016.02); *G01L 1/246* (2013.01); *A61B 2090/064* (2016.02)

(58) Field of Classification Search
CPC ..... G01I 1/246; A61B 90/06; A61B 2090/065
See application file for complete search history.

(56) References Cited

U.S. PATENT DOCUMENTS

| 4,906,907 A | 3/1990 | Tsuchihashi et al. |
| 5,624,398 A | 4/1997 | Smith et al. |

(Continued)

FOREIGN PATENT DOCUMENTS

| CA | 2709634 A1 | 7/2009 |
| DE | 1147411 B | 4/1963 |

(Continued)

OTHER PUBLICATIONS

Abe, Ilda et al., "Three-Parameter Simultaneous Measurement Using Superimposed Bragg Gratings in High-birefringence Optical Fibers", 16th International Conference on Optical Fiber Sensors, Oct. 13-17, 2003, Nara, Japan, 4 Pages.

(Continued)

*Primary Examiner* — Ronald Hupczey, Jr.

(57) ABSTRACT

A force sensing device is provided for use with a surgical instrument shaft having a two degree-of-freedom wrist mounted end effector portion having a working surface; a housing defines an annular collar sized to snugly fit about the two degree-of-freedom wrist and defines a cap sized to snugly fit about the end effector portion; an optical fiber including a segment is embedded within the annular collar and including a segment embedded within the cap; a first fiber Bragg grating (FBG) formed in the segment of the optical fiber embedded within the cap.

16 Claims, 11 Drawing Sheets

(56) References Cited

U.S. PATENT DOCUMENTS

| | | |
|---|---|---|
| 5,625,576 A | 4/1997 | Massie et al. |
| 5,784,542 A | 7/1998 | Ohm et al. |
| 5,855,583 A | 1/1999 | Wang et al. |
| 6,197,017 B1 | 3/2001 | Brock et al. |
| 6,331,181 B1 | 12/2001 | Tierney et al. |
| 6,394,998 B1 | 5/2002 | Wallace et al. |
| 6,459,926 B1 | 10/2002 | Nowlin et al. |
| 6,494,882 B1 | 12/2002 | Lebouitz et al. |
| 6,594,552 B1 | 7/2003 | Nowlin et al. |
| 6,817,974 B2 | 11/2004 | Cooper et al. |
| 6,879,880 B2 | 4/2005 | Nowlin et al. |
| 6,994,708 B2 | 2/2006 | Manzo |
| 7,083,571 B2 | 8/2006 | Wang et al. |
| 7,169,141 B2 | 1/2007 | Brock et al. |
| 7,935,130 B2 | 5/2011 | Williams |
| 8,004,229 B2 | 8/2011 | Nowlin et al. |
| 8,306,656 B1 | 11/2012 | Schaible et al. |
| 8,375,808 B2 | 2/2013 | Blumenkranz et al. |
| 8,444,631 B2 | 5/2013 | Yeung et al. |
| 8,479,969 B2 | 7/2013 | Shelton, IV |
| 8,506,555 B2 | 8/2013 | Ruiz Morales |
| 8,551,115 B2 | 10/2013 | Steger et al. |
| 8,602,288 B2 | 12/2013 | Shelton, IV et al. |
| 8,613,230 B2 | 12/2013 | Blumenkranz et al. |
| 8,620,473 B2 | 12/2013 | Diolaiti et al. |
| 8,622,935 B1 | 1/2014 | Leo |
| 8,628,518 B2 | 1/2014 | Blumenkranz et al. |
| 8,771,270 B2 | 7/2014 | Burbank |
| 8,800,838 B2 | 8/2014 | Shelton, IV |
| 8,945,095 B2 | 2/2015 | Blumenkranz et al. |
| 9,028,494 B2 | 5/2015 | Shelton, IV et al. |
| 9,113,904 B2 | 8/2015 | Kerr et al. |
| 9,204,923 B2 | 12/2015 | Manzo et al. |
| 9,232,979 B2 | 1/2016 | Parihar et al. |
| 9,671,860 B2 | 6/2017 | Ogawa et al. |
| 9,707,684 B2 | 7/2017 | Ruiz et al. |
| 9,782,214 B2 | 10/2017 | Houser et al. |
| 9,943,375 B2 | 4/2018 | Blumenkranz et al. |
| 9,952,107 B2 | 4/2018 | Blumenkranz et al. |
| 10,085,809 B2 | 10/2018 | Blumenkranz et al. |
| 10,130,366 B2 | 11/2018 | Shelton, IV et al. |
| 10,201,365 B2 | 2/2019 | Boudreaux et al. |
| 10,219,874 B2 | 3/2019 | Yu et al. |
| 10,238,458 B2 | 3/2019 | Verner et al. |
| 10,363,107 B2 | 7/2019 | Blumenkranz et al. |
| 10,398,433 B2 | 9/2019 | Boudreaux et al. |
| 10,595,836 B2 | 3/2020 | Smaby et al. |
| 10,595,887 B2 | 3/2020 | Shelton, IV et al. |
| 10,653,435 B2 | 5/2020 | Shelton, IV et al. |
| 10,682,141 B2 | 6/2020 | Moore et al. |
| 2005/0096502 A1 | 5/2005 | Khalili |
| 2005/0119527 A1 | 6/2005 | Banik et al. |
| 2005/0200324 A1 | 9/2005 | Guthart et al. |
| 2006/0020167 A1 | 1/2006 | Sitzmann |
| 2007/0018958 A1 | 1/2007 | Tavakoli et al. |
| 2007/0043338 A1 | 2/2007 | Moll et al. |
| 2007/0078484 A1 | 4/2007 | Talarico et al. |
| 2007/0119274 A1 | 5/2007 | Devengenzo et al. |
| 2007/0156019 A1 | 7/2007 | Larkin et al. |
| 2008/0046122 A1 | 2/2008 | Manzo et al. |
| 2008/0065105 A1 | 3/2008 | Larkin et al. |
| 2008/0132893 A1 | 6/2008 | D'Amelio et al. |
| 2008/0147090 A1* | 6/2008 | Seibold .................. A61B 34/71 606/130 |
| 2009/0088774 A1 | 4/2009 | Swarup et al. |
| 2009/0088775 A1 | 4/2009 | Swarup et al. |
| 2009/0324161 A1 | 12/2009 | Prisco |
| 2010/0063478 A1 | 3/2010 | Selkee |
| 2010/0313679 A1 | 12/2010 | Larkin et al. |
| 2011/0015632 A1 | 1/2011 | Artale |
| 2011/0046659 A1 | 2/2011 | Ramstein et al. |
| 2011/0071543 A1 | 3/2011 | Prisco et al. |
| 2011/0277775 A1 | 11/2011 | Holop et al. |
| 2011/0282356 A1 | 11/2011 | Solomon et al. |
| 2011/0295269 A1 | 12/2011 | Swensgard et al. |
| 2011/0295270 A1 | 12/2011 | Giordano et al. |
| 2012/0116391 A1 | 5/2012 | Houser et al. |
| 2012/0123441 A1 | 5/2012 | Au et al. |
| 2013/0291654 A1 | 11/2013 | Blumenkranz et al. |
| 2014/0005662 A1 | 1/2014 | Shelton, IV |
| 2014/0005678 A1 | 1/2014 | Shelton, IV et al. |
| 2014/0005708 A1 | 1/2014 | Shelton, IV |
| 2014/0052150 A1 | 2/2014 | Taylor et al. |
| 2014/0088614 A1* | 3/2014 | Blumenkranz ........... G01L 1/00 73/862.621 |
| 2014/0107627 A1 | 4/2014 | Blumenkranz et al. |
| 2014/0257333 A1 | 9/2014 | Blumenkranz |
| 2015/0135832 A1 | 5/2015 | Blumenkranz et al. |
| 2015/0150635 A1 | 6/2015 | Kilroy et al. |
| 2015/0164598 A1 | 6/2015 | Blumenkranz et al. |
| 2015/0374447 A1 | 12/2015 | Blumenkranz et al. |
| 2017/0007345 A1 | 1/2017 | Smith et al. |
| 2017/0165017 A1 | 6/2017 | Chaplin et al. |
| 2017/0172687 A1 | 6/2017 | Smith et al. |
| 2017/0215944 A1 | 8/2017 | Keffeler |
| 2017/0303996 A1 | 10/2017 | Kerr et al. |
| 2018/0042689 A1 | 2/2018 | Mozdzierz et al. |
| 2018/0078249 A1 | 3/2018 | Stoy et al. |
| 2019/0069966 A1 | 3/2019 | Petersen et al. |
| 2019/0094084 A1 | 3/2019 | Swinehart et al. |
| 2019/0125354 A1 | 5/2019 | Deck et al. |
| 2019/0142536 A1 | 5/2019 | Steger et al. |
| 2019/0175188 A1 | 6/2019 | Pv |
| 2019/0201018 A1 | 7/2019 | Shelton, IV et al. |
| 2019/0223960 A1 | 7/2019 | Chaplin et al. |
| 2019/0223966 A1 | 7/2019 | Holop et al. |
| 2019/0336228 A1 | 11/2019 | Blumenkranz et al. |
| 2020/0253669 A1 | 8/2020 | Diolaiti et al. |
| 2020/0278265 A1 | 9/2020 | Suresh |
| 2021/0022819 A1 | 1/2021 | Duque et al. |
| 2021/0045819 A1 | 2/2021 | Castillo et al. |
| 2021/0181048 A1 | 6/2021 | Lisiak |
| 2022/0401171 A1 | 12/2022 | Comenencia et al. |

FOREIGN PATENT DOCUMENTS

| | | |
|---|---|---|
| EP | 0590713 A2 | 4/1994 |
| EP | 2362285 A2 | 8/2011 |
| EP | 2431000 A2 | 3/2012 |
| JP | 9318469 A | 12/1997 |
| JP | 2002159509 A | 6/2002 |
| KR | 100778387 B1 | 11/2007 |
| WO | WO-2007143859 A1 | 12/2007 |
| WO | WO-2009123891 A1 | 10/2009 |
| WO | WO-2012166806 A1 | 12/2012 |
| WO | WO-2014151952 A1 | 9/2014 |
| WO | WO-2014172213 A2 | 10/2014 |
| WO | WO-2017064303 A1 | 4/2017 |
| WO | WO-2020102774 A1 | 5/2020 |
| WO | WO-2020102776 A1 | 5/2020 |
| WO | WO-2020102778 A1 | 5/2020 |
| WO | WO-2020102780 A1 | 5/2020 |
| WO | WO-2021076765 A1 | 4/2021 |
| WO | WO-2021097386 A1 | 5/2021 |

OTHER PUBLICATIONS

Abe, Ilda et al., "Characterization of FBGs written in Hibi IEC fibre for multiparameter sensors," 15th Annual Meeting of the IEEE Lasers and Electro-Optics Society, Nov. 10-14, 2002, vol. 1, pp. 173-174.

Betz, Daniel C. et al., "Advanced Layout of a Fiber Bragg Grating Strain Gauge Rosette," Journal of Lightwave Technology, vol. 24, No. 2, Feb. 2006, pp. 1019-1026.

Cavaleiro, P.M. et al., "Simultaneous Measurement of Strain and Temperature Using Bragg Gratings Written in Germanosilicate and Boron-Codoped Germanosilicate Fibers," IEEE Photonics Technology Letters, vol. 11, No. 12, Dec. 1999, pp. 1635-1637.

Cepolina F. et al., "Review of robotic fixtures for minimally invasive surgery," International Journal of Medical Robotics and Computer Assisted Surgery, 2004, pp. 43-63, vol. 1, Issue-1.

(56) References Cited

OTHER PUBLICATIONS

Chen, Guanghui et al., "Simultaneous Strain and Temperature Measurements With Fiber Bragg Grating Written in Novel Hi-Bi Optical Fiber," IEEE Photonics Technology Letters, vol. 16, No. 1, pp. 221-223, Jan. 2004.
Davis, M.A. and A.D. Kersey, "Simultaneous measurement of temperature and strain using fibre Bragg gratings and Brillouin scattering," IEE Proceedings Optoelectron., vol. 144, No. 3, pp. 151-155, Jun. 1997.
Du, Wei-Chong et al., "Fiber Bragg Grating Cavity Sensor for Simultaneous Measurement of Strain and Temperature," IEEE Photonics Technology Letters, vol. 11, No. 1, pp. 105-107, Jan. 1999.
Du, Wei-Chong et al., "Temperature Independent Strain Measurement with a Fiber Grating Tapered Cavity Sensor," IEEE Photonics Technology Letters, vol. 11, No. 5, pp. 596-598, May 1999.
Echevarria, J. et al., "Efficient Temperature and Strain Discrimination with a Single Type I Fiber Bragg Grating Transducer," 13th Annual Meeting IEEE Lasers and Electro-Optics Sociey 2000 Annual Meeting (LEOS-2000), Nov. 13-16, 2000, vol. 2, pp. 458-459.
Echevarria, J. et al., "Uniform Fiber Bragg Grating First- and Second-Order Diffraction Wavelength Experimental Characterization for Strain-Temperature Discrimination," IEEE Photonics Technology Letters, vol. 13, No. 7, pp. 696-698, Jul. 2001.
Frank, Andreas et al., "Novel Methods for Simultaneous Strain and Temperature Measurements with Optical Fiber Bragg Gratings," SPIE Conference on Fiber Optic Sensor Technology and Applications, Boston, Massachusetts, Sep. 1999, SPIE vol. 3860, pp. 89-97.
Frazao, O. and J.L. Santos, "Simultaneous measurement of strain and temperature using a Bragg grating structure written in germanosilicate fibres," Journal of Optics A: Pure and Applied Optics, vol. 6, pp. 553-556, 2004.
Frazao, O. et al., "Sampled fibre Bragg grating sensors for simultaneous strain and temperature measurement," Electronics Letters, Jul. 4, 2002, vol. 38, No. 14, 2 Pages.
Frazao, O. et al., "Discrimination of strain and temperature using Bragg gratings in microstructured and standard optical fibres," Measurement Science and Technology, vol. 16, pp. 2109-2113, 2005.
Frazao, O. et al., "Short in-fibre Bragg grating structure for simultaneous measurement of strain and temperature," 17th International Conference on Optical Fibre Sensors, Proceedings of SPIE, vol. 5855, pp. 876-879, 2005.
Frazao, O. et al., "Simultaneous measurement of strain and temperature using fibre Bragg gratings in a twisted configuration," Journal of Optics A: Pure and Applied Optics, vol. 7, pp. 427-430, 2005.
Frazao, O et al., "Simultaneous measurement of strain and temperature using type I and type IIA fibre Bragg gratings," Journal of Optics A: Pure and Applied Optics, vol. 5, pp. 183-185, 2003.
Frazao, O. et al., "Simultaneous measurement of termperature and strain using a step spectrum profile fibre Bragg grating arrangement," 2nd European Workshop on Optical Fibre Sensors, Eds. Lopez-Higuera et al., 2004, SPIE vol. 5502, pp. 132-135.
Frazao, O. et al., "Strain-temperature discrimination using a step spectrum profile fibre Bragg grating arrangement," Sensors and Actuators A: Physical, vol. 120, Issue 2, May 17, 2005, pp. 490-493.
Guan, Bai-Ou et al., "Cladding mode effect in superstructure fiber Bragg gratings and its applications in simultaneous strain and temperature measurement," Optical Fiber Communication Conference and Exhibit (OFC-2001), 2001, vol. 3, pp. WDD79-1-WDD79-3.
Guan, Bai-Ou et al., "Simultaneous strain and temperature measurement using a single fibre Bragg grating," Electronics Letters, Jun. 8, 2000, vol. 36, No. 12, pp. 1018-1019.
Guan, Bai-Ou et al., "Simultaneous Strain and Temperature Measurement Using a Superstructure Fiber Bragg Grating," IEEE Photonics Technology Letters, vol. 12, No. 6, pp. 675-677, Jun. 2000.
Guo, Tuan et al., "Temperature-Insensitive Fiber Bragg Grating Force Sensor via a Bandwidth Modulation and Optical-Power Detection Technique," Journal of Lightwave Technology, vol. 24, No. 10, pp. 3797-3802, Oct. 2006.
Gwandu, B.A.L. and W. Zhang, "Tailoring the temperature responsivity of fibre Bragg gratings," Proceedings of IEEE Sensors, Oct. 24-27, 2004, vol. 3, pp. 1430-1433.
Gwandu, B.A.L. et al., "Simultaneous Measurement of Strain, Temperature and Curvature Using a Sampled Fibre Bragg Grating," 15th Optical Fiber Sensors Conference (OFS 2002) Technical Digest, May 6-10, 2002, vol. 1, pp. 79-82.
Han, Kyung Jun et al., "Simultaneous Measurement of Strain and Temperature Incorporating a Long-Period Fiber Grating Inscribed on a Polarization-Maintaining Fiber," IEEE Photonics Technology Letters, vol. 16, No. 9, pp. 2114-2116, Sep. 2004.
Han, Young-Geun and Sang Bae Lee, "Simultaneous measurement of temperature and strain using dual long-period fiber gratings with controlled temperature and strain sensitivities," Optics Express, vol. 11, No. 5, pp. 476-481, Mar. 10, 2003.
Haran, Frank M. et al., "Rapid Communication: A strain-isolated fibre Bragg grating sensor for temperature compensation of fibre Bragg grating strain sensors," Measurement Science and Technology, vol. 9, pp. 1163-1166, 1998.
Hazel D., "Comparing Strain Gage Measurements to Force Calculations in a Simple Cantilever Beam," Worcester Polytechnic Institute Major Qualifying Project, Jan. 27, 2016, 39 pages.
Hitz, Breck, "Wrinkles improve fiber optic strain sensor," Photonics Technology News, Jan. 2007, 3 Pages.
James, S.W. et al., "Simultaneous independent temperature and strain measurement using in-fibre Bragg grating sensors," Electronic Letters, vol. 32, No. 12, pp. 1133-1134, Jun. 6, 1996.
Jung, Jaehoon et al., "Simultaneous measurement of strain and temperature by use of a single-fiber Bragg grating and an erbium-doped fiber amplifier," Applied Optics, vol. 38, No. 13, pp. 2749-2751, May 1, 1999.
Jung, Jaehoon et al., "Simultaneous measurement of strain and temperature using a single fiber Brag grating written in an erbium:ytterblum-doped fiber," Summaries of papers presented at the Conference on Lasers and Electro-Optics (CLEO'99), May 23-28, 1999, p. 386.
Kaczmarek, Cesary et al., "Fiber Bragg Grating Differential Strain Sensor," 7th International Conference, "The Experience of Designing and Application of CAD Systems in Microelectronics" (CADSM'2003), Feb. 18-22, 2003, Lviv-Slaske, Ukraine, pp. 172-174.
Kalli, K. et al., Abstract of "Development of an electrically tuneable Bragg grating filter in polymer optical fibre operating at 1.55 μm," Measurement Science and Technology, vol. 18, p. 3155, 2007.
Kalli, Kyriacos et al., "Possible approach for the simultaneous measurement of temperature and strain via first and second order diffraction from Bragg grating sensors," SPIE vol. 2507, pp. 190-198, 1995.
Kanellopoulos, Sotiris E. et al., "Simultaneous strain and temperature sensing with photogenerated in-fiber gratings," Optics Letters, vol. 20, No. 3, pp. 333-335, Feb. 1, 1995.
Kang, Hyun-Kyu et al., "Simultaneous Measurement of Strain and Temperature of Structures Using Fiber Optic Sensor," Journal of Intelligent Material Systems and Structures, vol. 12, pp. 277-281, Apr. 2001.
Kim, Sungchul et al., "Temperature-independent strain sensor using a chirped Bragg grating partially embedded in a glass tube," 12th Annual Meeting IEEE Lasers and Electro-Optics Socienty (LEOS'99), Nov. 8-11, 1999, vol. 2, pp. 878-879.
Koyamada, Yahei et al., "Novel Fiber-Optic Distributed Strain and Temperature Sensor with Very High Resolution," IEICE Transactions on Communications, vol. E89-B, No. 5, pp. 1722-1725, May 2006, IEICE Communications Society, Japan.
Lim, Jirapong et al. "Strain and Temperature Sensors Using Multimode Optical Fiber Bragg Gratings and Correlation Signal Processing," IEEE Transactions on Instrumentation and Measurement, vol. 51, No. 4, pp. 622-627, Aug. 2002.

(56) References Cited

OTHER PUBLICATIONS

Mandal, Jharna et al., "Bragg grating tuned fiber laser system for measurement of wider range temperature and strain," Optics Communications, vol. 244, pp. 111-121, 2005.
Measures, Raymond M., "Fiber Optic Strain Sensing," in Fiber Optic Smart Structures, Ed. Eric Udd, Apr. 1995, Wiley, pp. 208-209.
Mertmann M., et al., "Grippers for the Micro Assembly Containing Shape Memory Actuators and Sensors," Le Journal de Physique IV France, vol. 7, Institut fuer Werstoffe, Ruhr-Universitaet, Bochum, Germany, Nov. 1997, pp. C5-621-C5-626.
Oh, S.T et al., "Discrimination of temperature and strain with a single FBG based on the birefringence effect," Optics Express, vol. 12, No. 4, pp. 724-729, Feb. 23, 2004.
Park Y.L., et al., "Force Sensing Robot Fingers using Embedded Fiber Bragg Grating Sensors and Shape Deposition Manufacturing," IEEE International Conference on Robotics and Automation, Apr. 2007, pp. 1510-1516.
Peirs, Jan et al., "A micro optical force sensor for force feedback during minimally invasive robotic surgery," Sensors and Actuators A, 2004, pp. 447-455, vol. 115.
Posey Jr., Ralph and Sandeep T. Vohra, "An Eight-Channel Fiber-Optic Bragg Grating and Stimulated Brillouin Sensor System for Simultaneous Temperature and Strain Measurements," IEEE Photonics Technology Letters, vol. 11, No. 12, pp. 1461-1643, Dec. 1999.
Rego, G. et al., "Simultaneous measurement of temperature and strain based on arc-induced long-period fibre gratings," Electronics Letters, Jan. 20, 2005, vol. 41 No. 2, pp. 60-62.
Seibold, Ulrich et al., "A 6-Axis force/torque sensor design for haptic feedback in minimally invasive robotic surgery," In: Proceedings of the 2nd VDE World Microtechnologies, 2003, 6 Pages.
Shu, X. et al., "Fiber grating type dependence of temperature and strain coefficients and application to simultaneous temperature and strain measurement," 15th Optical Fiber Sensors Conference (OFS 2002) Technical Digest, May 6-10, 2002, vol. 1, pp. 83-86.
Shu, Xuewen et al., "Dependence of temperature and strain coefficients on fiber grating type and its application to simultaneous temperature and strain measurement," Optics Letters, vol. 27, No. 9, pp. 701-703, May 1, 2002.
Shu, Xuewen et al., "Effectively simultaneous temperature and strain measurement utilising a dual-grating sensor formed by Type IA and Type IIA FBGs," p. 1, 2002.
Silva-Lopez, Manuel et al., "Strain and temperature sensitivity of a single-mode polymer optical fiber," Optics Letters, vol. 30, No. 23, pp. 3129-3131, Dec. 1, 2005.
Sivanesan, Ponniah, "Optical Fiber Sensor for Simultaneous Measurement of Distributed Strain and Temperature," Ph.D. Dissertation, University of Maryland College Park, Department of Physics, pp. 1-51, 2002.
Trpkovski, S. et al., "Dual temperature and strain sensor using a combined fiber Bragg grating and fluorescence intensity ratio technique in $Er^{3+}$-doped fiber," Review of Scientific Instruments, vol. 74, No. 5, pp. 2880-2885, May 2003.
Wade, S.A. et al., "Fiber optic sensor for dual measurement of temperature and strain using a combined fluorescence lifetime decay and fiber Bragg grating technique," Review of Scientific Instruments, vol. 72, No. 8, pp. 3186-3190, Aug. 2001.
Wong, Allan C. L. et al., "Multiplexed fibre Fizeau interferometer and fibre Bragg grating sensor system for simultaneous measurement of quasi-static strain and temperature using discrete wavelet transform," Measurement Science and Technology, 2006, pp. 384-392, vol. 17—Issue 2, Institute of Physics Publishing.
Xu, M.G. et al., "Discrimination between strain and temperature effects using dual-wavelength fibre grating sensors," Electronic Letters, vol. 30, No. 13, pp. 1085-1087, Jun. 23, 1994.
Xu, M.G. et al., "Temperature-independent strain sensor using a chirped Bragg grating in a tapered optical fibre," Electronic Letters, vol. 31, No. 10, pp. 823-825, May 11, 1995.
Yang, Bin et al., "Fibre Bragg Grating Sensor for Simultaneous Measurement of Strain and Temperature," Journal of Industrial Textiles, vol. 34, No. 2, pp. 97-115, Oct. 2004.
Zhang, L. et al., "Advances in UV-inscribed fiber grating optic sensor technologies," Proceedings of IEEE Sensors, Jun. 12-14, 2002, vol. 1, pp. 31-35.
Zhang, Lin et al., "Advanced optical sensing techniques using novel fibre gratings," Proceedings of 2002 IEEE/LEOS Workshop on Fibre and Optical Passive Components, Jun. 5- 6, 2002, pp. 65-74.
International Preliminary Report on Patentability for Application No. PCT/US2019/033986, dated Dec. 10, 2020, 7 pages.
International Search Report and Written Opinion for Application No. PCT/US2019/033986, dated Sep. 19, 2019, 21 pages (ISRG09620/PCT).
Vertut. Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

FIBER BRAGG GRATING END EFFECTOR FORCE SENSOR

CLAIM OF PRIORITY

This application is a U.S. National Stage Filing under 35 U.S.C. 371 from International Application No. PCT/US2019/033986, filed on May 24, 2019, and published as WO 2019/227032 A1 on Nov. 28, 2019, which claims the benefit of priority to U.S. Patent Application Ser. No. 62/676,653, filed on May 25, 2018, each of which is incorporated by reference herein in its entirety.

BACKGROUND

Minimally invasive medical techniques are intended to reduce the amount of tissue that is damaged during diagnostic or surgical procedures, thereby reducing patient recovery time, discomfort, and deleterious side effects. Teleoperated surgical systems that use robotic technology (so-called surgical robotic systems) may be used to overcome limitations of manual laparoscopic and open surgery. Advances in telepresence systems provide surgeons views inside a patient's body, an increased number of degrees of motion of surgical instruments, and the ability for surgical collaboration over long distances. In manual minimally invasive surgery, surgeons feel the interaction of the instrument with the patient via a long shaft, which eliminates tactile cues and masks force cues. In teleoperation surgery systems, natural force feedback is largely eliminated because the surgeon no longer manipulates the instrument directly. Kinesthetic or force feedback systems typically measure or estimate the forces applied to the patient by the surgical instrument.

SUMMARY

In one aspect, a force sensing device is provided for use with a surgical instrument shaft having a two degree-of-freedom wrist mounted end effector portion having a working surface. A housing defines an annular collar sized to snugly fit about the two degree-of-freedom wrist and defines a cap sized to snugly fit about the end effector portion. An optical fiber including a segment is embedded within the annular collar and including a segment embedded within the cap. A first fiber Bragg grating (FBG) formed in the segment of the optical fiber embedded within the cap.

In another aspect, a surgical instrument includes an elongated shaft, a two-degree of freedom wrist, and an end effector that includes first and second articulable jaws mounted to the wrist. A removable housing formed of a flexible material that defines an annular collar snugly fit about the wrist and that defines a cap snugly fit about the first jaw. An optical fiber includes a segment embedded within the annular collar and includes a segment embedded within the cap. A first fiber Bragg grating (FBG) is formed in the segment of the optical fiber embedded within the cap.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

SUMMARY

Description of Embodiments

Teleoperated Surgical System

Figure 1:
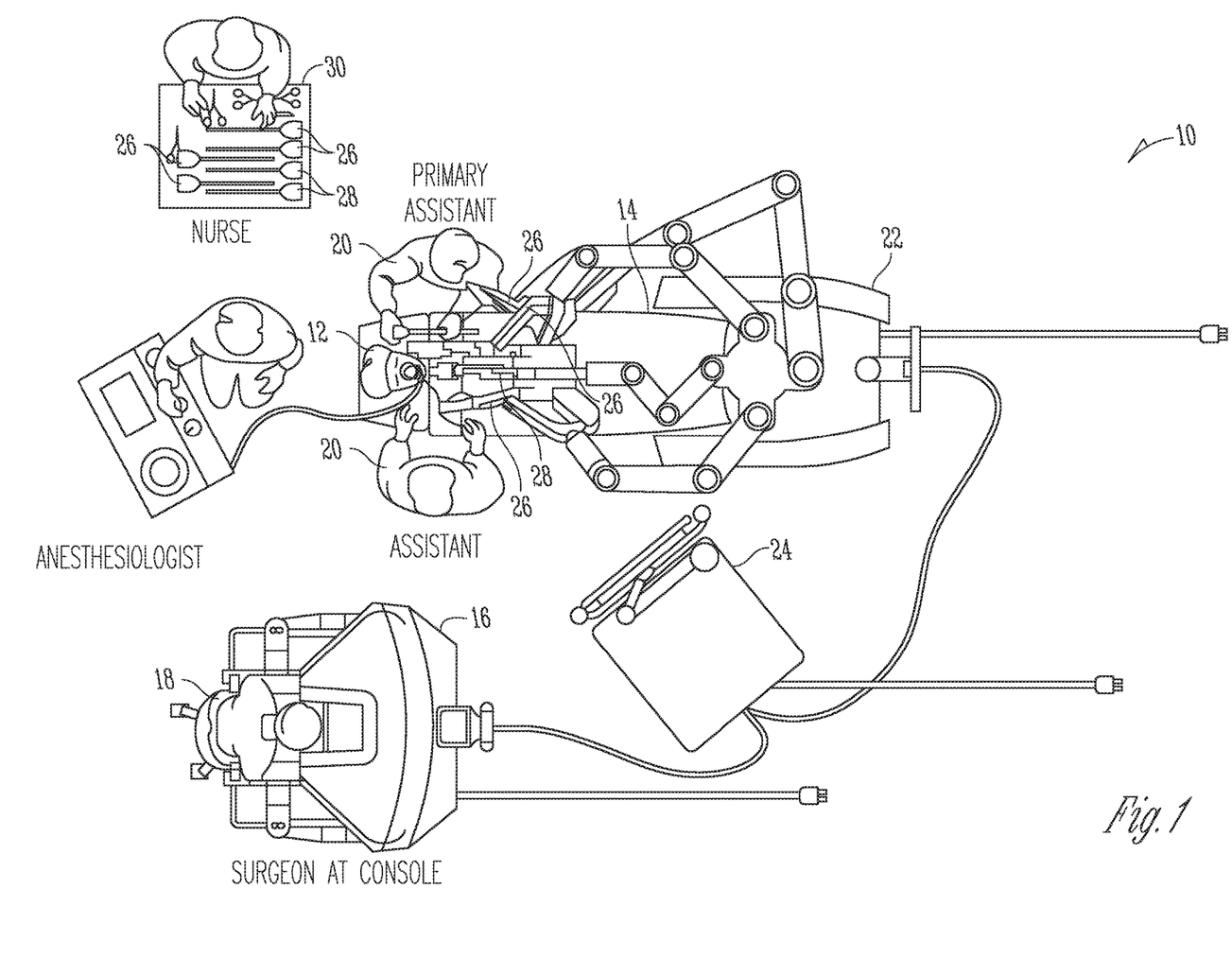
FIG. 1 is an illustrative plan view of a minimally invasive teleoperated surgical system.

FIG. 1 is an illustrative plan view of a minimally invasive teleoperated surgical system 10 for performing a minimally invasive diagnostic or surgical procedure on a patient 12 who is lying on an operating table 14. The system includes a surgeon's console 16 for use by a surgeon 18 during the procedure. One or more assistants 20 may also participate in the procedure. The minimally invasive teleoperated surgical system 10 further includes one or more patient-side cart 22 and an electronics cart 24. The patient-side cart 22 can manipulate at least one surgical instrument 26 through a minimally invasive incision in the body of the patient 12 while the surgeon 18 views the surgical site through the surgeon's console 16. An image of the surgical site can be obtained by an endoscope 28, such as a stereoscopic endoscope, which may be manipulated by the patient-side cart 22 to orient the endoscope 28. Computer processors located on the electronics cart 24 may be used to process the images of the surgical site for subsequent display to the surgeon 18 through the surgeon's console 16. In some embodiments, stereoscopic images may be captured, which allow the perception of depth during a surgical procedure. The number of surgical instruments 26 used at one time will generally depend on the diagnostic or surgical procedure and the space constraints within the operative site among other factors. If it is necessary to change one or more of the surgical instruments 26 being used during a procedure, an assistant 20 may remove the surgical instrument 26 from the patient-side cart 22, and replace it with another surgical instrument 26 from a tray 30 in the operating room.

Figure 2:
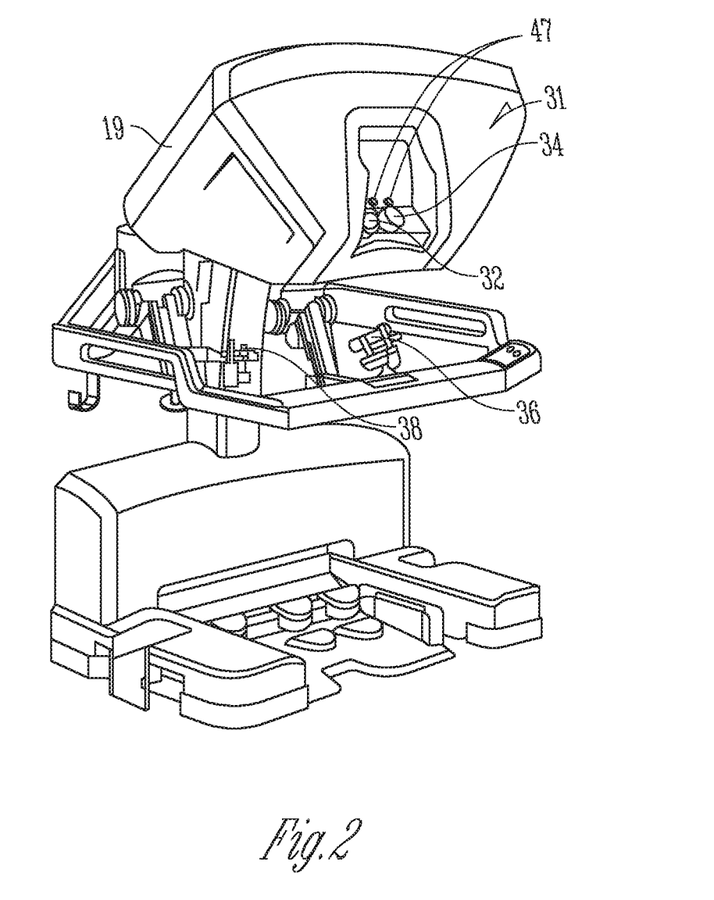
FIG. 2 is a perspective view of the surgeon's console of the minimally invasive teleoperated surgical system of FIG. 1.

FIG. 2 is a perspective view of the surgeon's console 16. The surgeon's console 16 includes a viewer display 31 that includes a left eye display 32 and a right eye display 34 for presenting the surgeon 18 with a coordinated stereoscopic view of the surgical site that enables depth perception. The console 16 further includes one or more hand-operated control inputs 36 to receive the larger-scale hand control movements. One or more surgical instruments installed for use on the patient-side cart 22 move in smaller-scale distances in response to surgeon 18's larger-scale manipulation of the one or more control inputs 36. The control inputs 36 may provide the same mechanical degrees of freedom as their associated surgical instruments 26 to provide the surgeon 18 with telepresence, or the perception that the control inputs 36 are integral with the instruments 26 so that the surgeon has a strong sense of directly controlling the instruments 26. To this end, position, force, and tactile feedback sensors (not shown) may be employed to transmit position, force, and tactile sensations from the surgical instruments 26 back to the surgeon's hands through the control inputs 36, subject to communication delay constraints.

Figure 3:
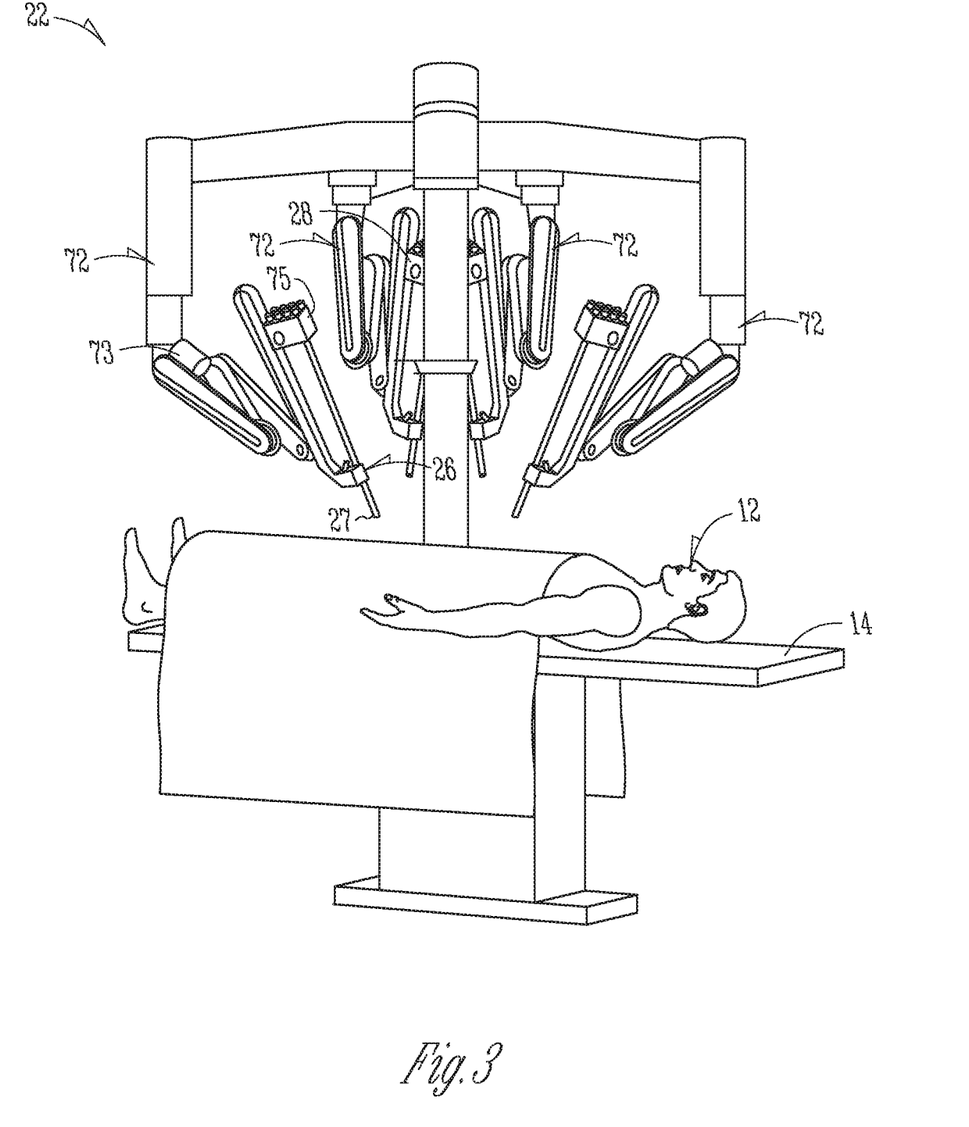
FIG. 3 is a perspective view of a patient-side cart of a minimally invasive teleoperated surgical system of FIG. 1.

FIG. 3 is a perspective view of a patient-side cart 22 of a minimally invasive teleoperated surgical system 10, in accordance with embodiments. The patient-side cart 22 includes four mechanical support arms 72. A surgical instrument manipulator 73, which includes motors to control instrument motion, is mounted at the end of each support arm assembly 72. Additionally, each support arm 72 can optionally include one or more setup joints (e.g., unpowered and/or lockable) that are used to position the attached surgical instrument manipulator 73 in relation to the patient for surgery. While the patient-side cart 22 is shown as including four surgical instrument manipulators 73, more or fewer surgical instrument manipulators 73 may be used. A teleoperated surgical system will generally include a vision system that typically includes a endoscopic camera instrument 28 for capturing video images and one or more video displays for displaying the captured video images.

In one aspect, for example, individual surgical instruments 26 and a cannulas 27 are removably coupled to manipulator 73, with the surgical instrument 26 inserted through the cannula 27. One or more teleoperated actuator motors of the manipulator 73 move the surgical instrument 26 as a whole. The manipulator 73 further includes an instrument carriage 75. The surgical instrument 26 is detachably connected to the instrument carriage 75. In one aspect, the instrument carriage 75 houses one or more teleoperated actuator motors (not shown) inside that provide a number of controller motions that the surgical instrument 26 translates into a variety of movements of an end effector on the surgical instrument 26. Thus, the teleoperated actuator motors in the instrument carriage 75 move only one or more components of the surgical instrument 26 rather than the instrument as a whole. Inputs to control either the instrument as a whole or the instrument's components are such that the input provided by a surgeon or other medical person to the control input (a "master" command) is translated into a corresponding action by the surgical instrument (a "slave" response). A wire cable-based force transmission mechanism or the like is used to transfer the motions of each of the remotely located teleoperated actuator motors to a corresponding instrument-interfacing actuator output located on instrument carriage 75. In some embodiments, the surgical instrument 26 is mechanically coupled to a first actuator motor, which controls a first motion of the surgical instrument such as longitudinal (z-axis) rotation. The surgical instrument 26 is mechanically coupled to a second actuator, which controls second motion of the surgical instrument such as two-dimensional (x, y) motion. The surgical instrument 26 is mechanically coupled to a third actuator, which controls third motion of the surgical instrument such as opening and closing of an end effector such as articulable jaws, i.e. jaws that can open and close, for example.

Figure 4:
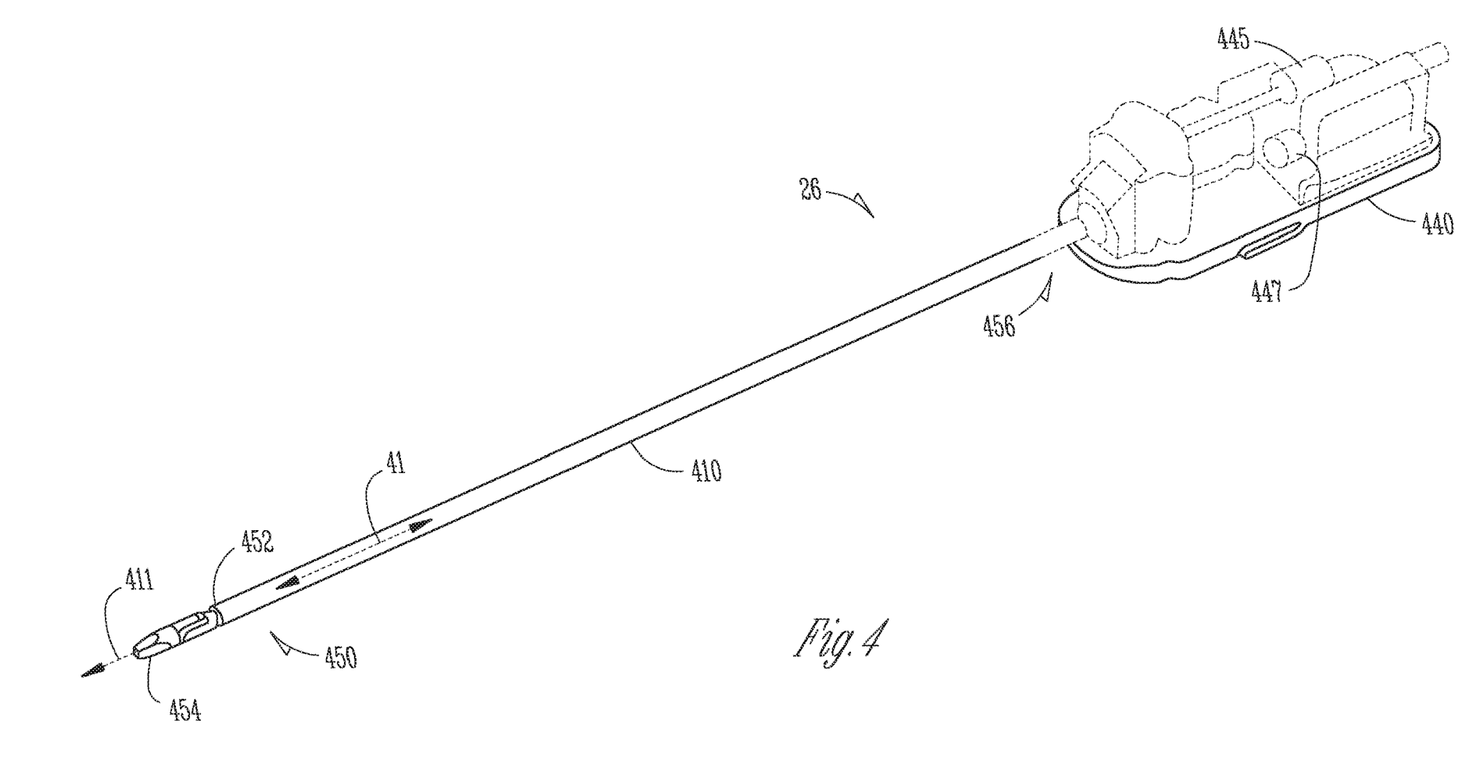
FIG. 4 is a perspective view of a surgical instrument used with the minimally invasive teleoperated surgical system of FIG. 1.

FIG. 4 is a perspective view of a surgical instrument 26, which includes an elongated hollow tubular shaft 410 having a centerline longitudinal axis 411, a distal (first) end portion 450 for insertion into a patient's body cavity and proximal (second) end portion 456 coupled adjacent a control mechanism 440 that includes multiple actuator motors 445, 447 (shown with dashed lines) that exert force upon wire cables coupled to impart motion to the end effector such as opening or closing of jaws and (x, y) wrist motion of a wrist. The surgical instrument 26 is used to wily out surgical or diagnostic procedures. The distal portion 450 of the surgical instrument 26 can provide any of a variety of end effectors 454, such as the forceps shown, a needle driver, a cautery device, a cutting tool, an imaging device (e.g., an endoscope or ultrasound probe), or the like. The surgical end effector 454 can include a functional mechanical degree of freedom, such as jaws that open or close, or a knife that translates along a path or a wrist that may move in x and y directions. In the embodiment shown, the end effector 454 is coupled to the elongated hollow shaft 410 by a wrist 452 that allows the end effector to be oriented relative to the elongate tube centerline axis 411. The control mechanism 440 controls movement of the overall instrument and the end effector at its distal portion.

End Effector Mounted on a Two
Degree-of-Freedom Wrist

Figure 5A:
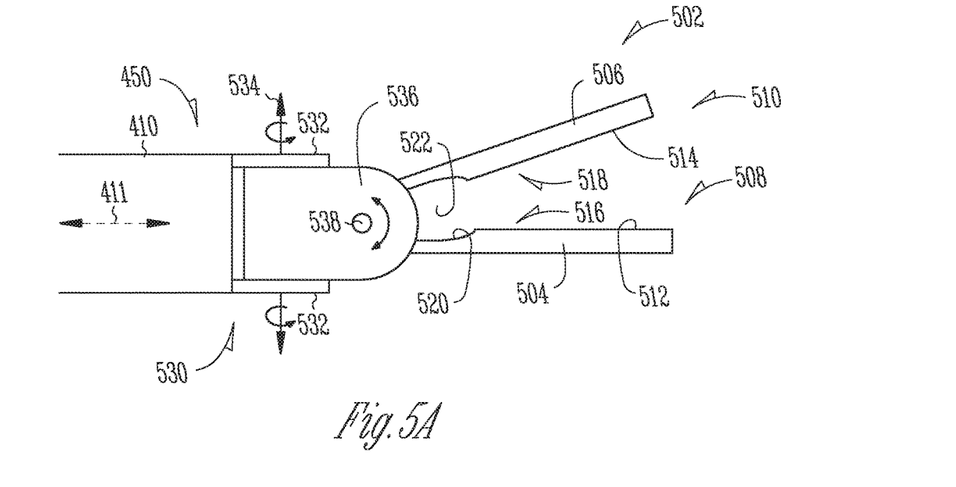
FIGS. 5A-5B are illustrative side views of an end effector having a pair of jaws at a distal end of a surgical instrument shaft in alignment with a central axis of the shaft.
Figure 5B:
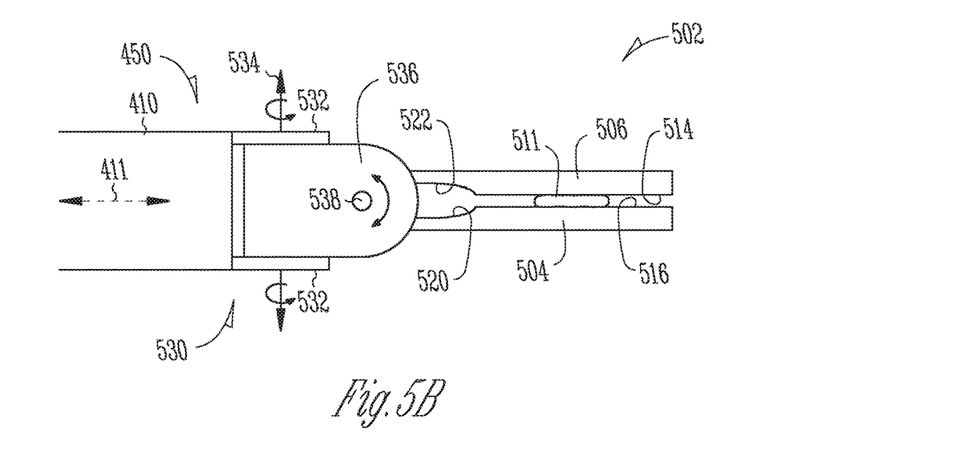

FIGS. 5A-5B are illustrative side views of an end effector 502 having a pair of jaws at a distal end 450 of a surgical instrument shaft 410 in alignment with a central axis 411 of the shaft 410. FIG. 5A shows first and second jaws 504, 506 in an open position. FIG. 5B shows the first and second jaws in a closed position. Distal portions 508, 510 of the first and second jaws include opposed facing working surfaces 512, 514 that may contact and grip anatomical tissue 511 between them as shown in FIG. 5B, for example. Proximal portions 516, 518 of the first and second jaws 504, 506 also include opposed facing non-working surfaces 520, 522 that do not contact each other during and that ordinarily do not engage tissue during normal operation. In some embodiments, the opposed facing non-working surface 520, 522s are recessed from the opposed facing working surfaces 512, 514.

Figure 6:
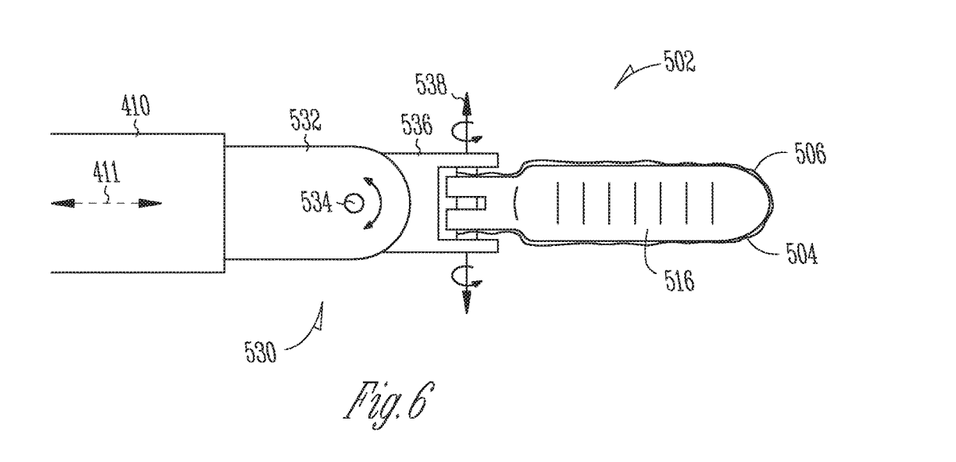
FIG. 6 is a top elevation partially transparent view of the end effector.

FIG. 6 is atop elevation partially transparent view of the end effector 502 of FIGS. 5A-5B. The second jaw is shown transparent in FIG. 6 so that a working surface 516 of the first jaw 504 is visible even though it actually is located behind the second jaw. The second jaw 506 is indicted by dashed lines in FIG. 6.

A two degree-of-freedom (2-dof) wrist mechanism 530 mounts the end effector jaws 504, 506 to the distal portion 450 of the shaft 410. The wrist 530 includes a proximal clevis 532 to permit rotation of the jaws about a first pivot axis 534. The wrist 530 includes a distal clevis 536 to permit rotation of the jaws 504, 506 about a second pivot axis 538. The distal clevis 536 is mounted for rotation about the first pivot axis 534 and the jaws 504, 506 are mounted for rotation about the second pivot axis 538. It will be appreciated that the jaws 504, 506 move between open and closed positions independent of their orientation about the first and second pivot axes 534, 538. Additional details of an embodiment of the example wrist mechanism 530 that includes proximal a clevis and a distal clevis are provided in FIGS. 5-7 and corresponding portions of the disclosure of U.S. Pat. No. 6,394,998, entitled, "Surgical Tools for Use in Minimally Invasive Telesurgical Applications".

Figure 7:
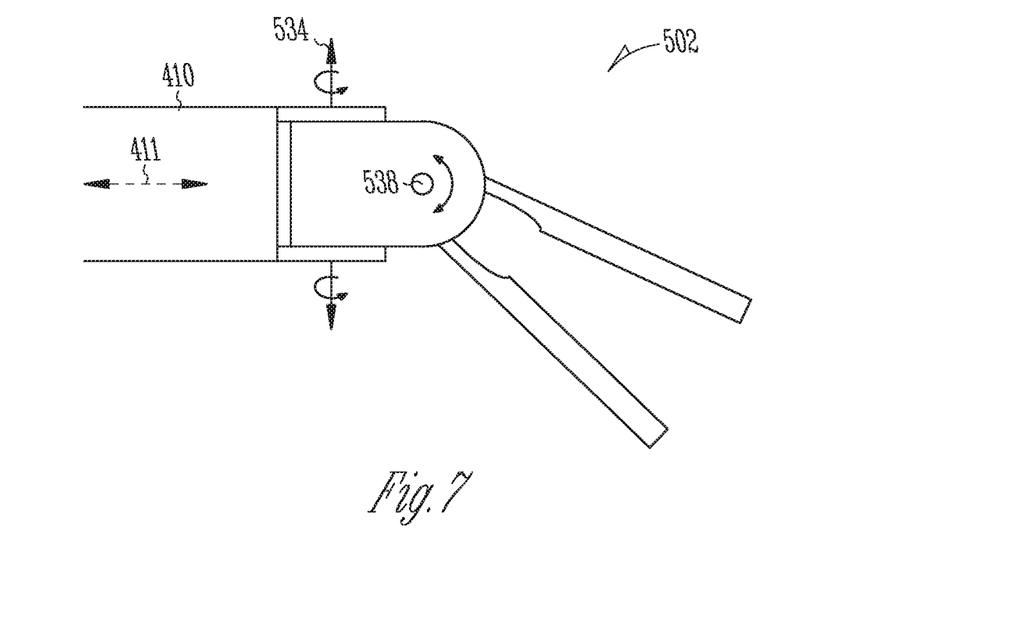
FIG. 7 is an illustrative side view of the end effector showing the end effector jaws rotated about the distal pivot axis to be non-aligned with the shaft center axis.
Figure 8:
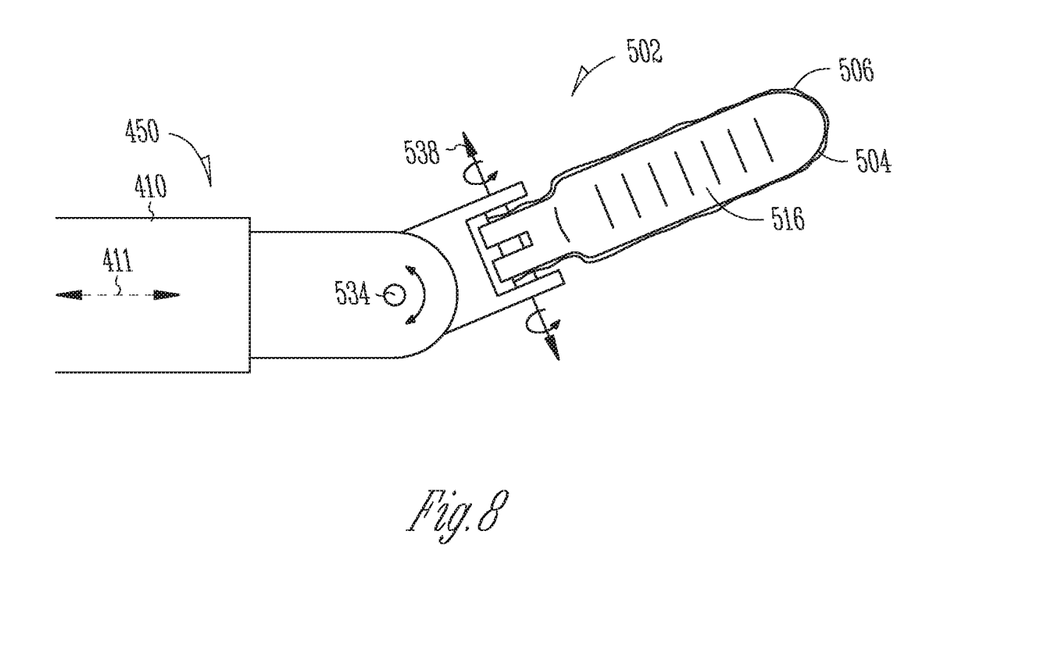
FIG. 8 is a top elevation partially transparent view of the end effector showing the end effector jaws rotated about the proximal pivot axis to be non-aligned with the shaft center axis.

FIG. 7 is an illustrative side view of the end effector 502 showing the end effector jaws 504, 506 in an open position and rotated about the distal pivot axis 538 to be non-aligned with the shaft center axis 411. FIG. 8 is a top elevation partially transparent view of the end effector 502, with the second jaw shown transparent, in which the end effector jaws 504, 506 are rotated about the proximal pivot axis 534 to be non-aligned with the shaft center axis 411.

FBG Force Sensor Device

Figure 9A:
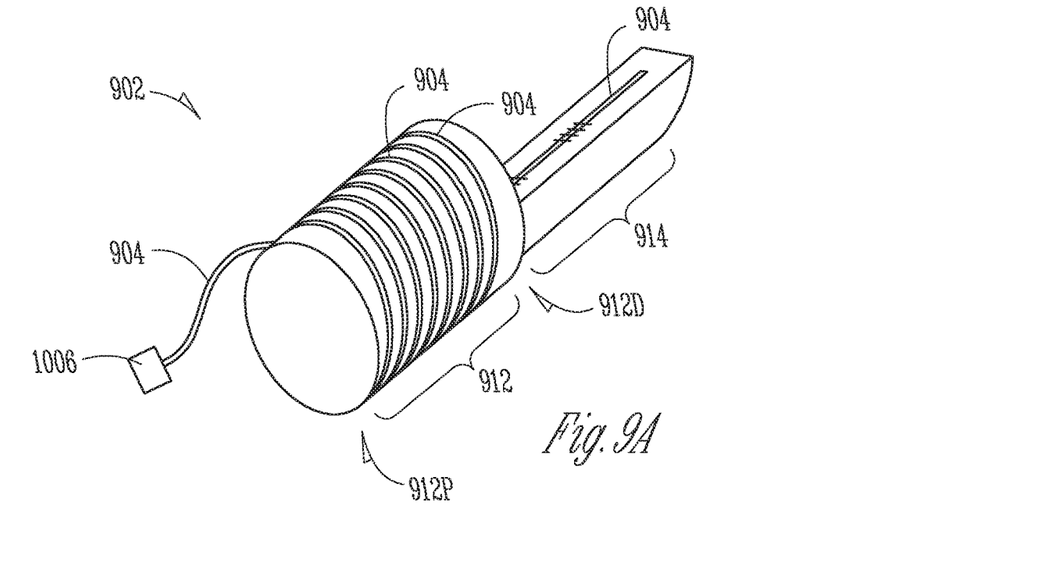
FIGS. 9A-9B provide an illustrative distal perspective view (FIG. 9A) and proximal perspective view (FIG. 9B) of a fiber Bragg grating force sensor device in accordance with some embodiments.
Figure 9B:
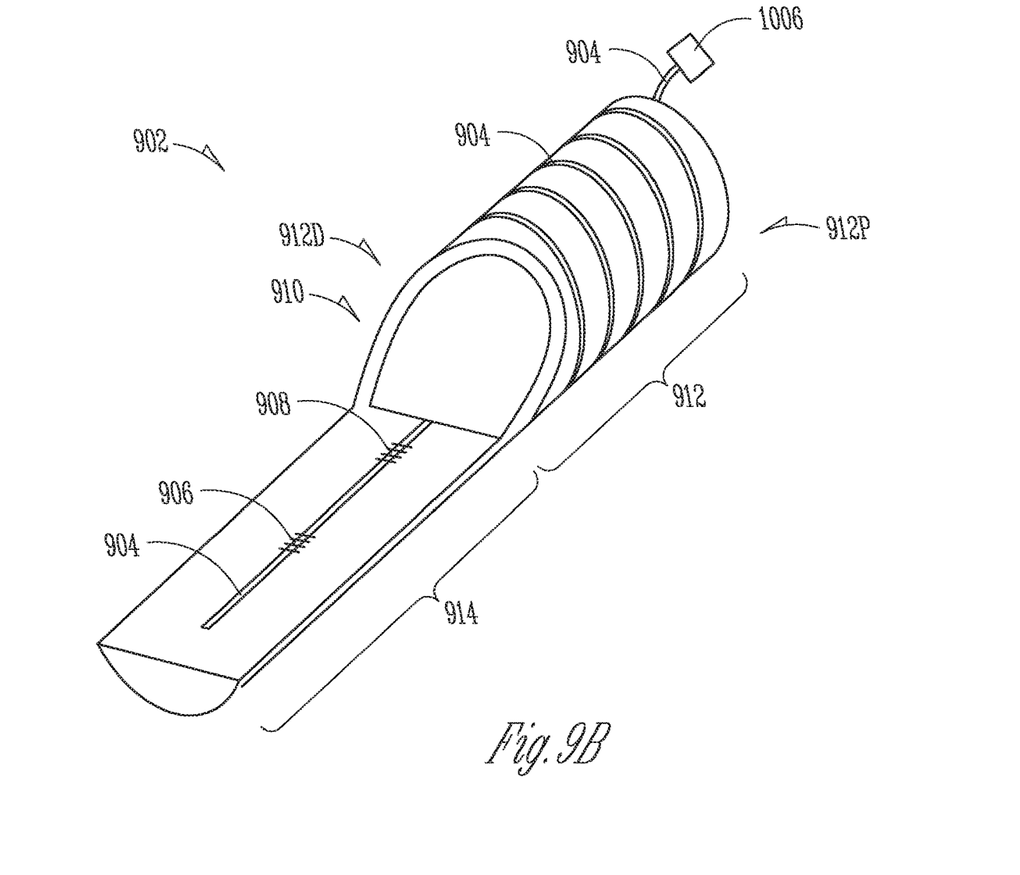

FIGS. 9A-9B provide an illustrative distal perspective view (FIG. 9A) and proximal perspective view (FIG. 9B) of a fiber Bragg grating (EBG) force sensor device 902 in accordance with some embodiments. The FBG force sensor device includes an optical fiber 904 that includes first and second FBGs 906, 908 embedded within a housing 910. The housing 910 may be formed of a flexible material. In some embodiments, the housing 910 may be formed of a thermoplastic elastomer or silicone rubber or a deformable material such as a polyester film or a plastic sheet, for example. The housing 910 includes an integral structure that includes an annular collar portion 912 and an elongated cantilever cap portion 914. The collar 912 includes a proximal collar portion 912p and a distal collar portion 912d. The cap 914 extends distally from the distal collar portion 912d. An optical fiber 904 is embedded within walls of the housing 910.

The FBG force sensor device 902 may be installed upon the surgical instrument end effector 502 for use to sense force during a surgical or diagnostic procedure. Following the procedure, the FBG force sensor 902 device may be removed from the end effector 502 and may be discarded. The surgical instrument 26 with the FBG sensor device 902 removed, may be sanitized though an auto clave process, for example, and a new replacement FBG force sensor device 902 may be installed on it for use in during a subsequent procedure.

Figure 10A:
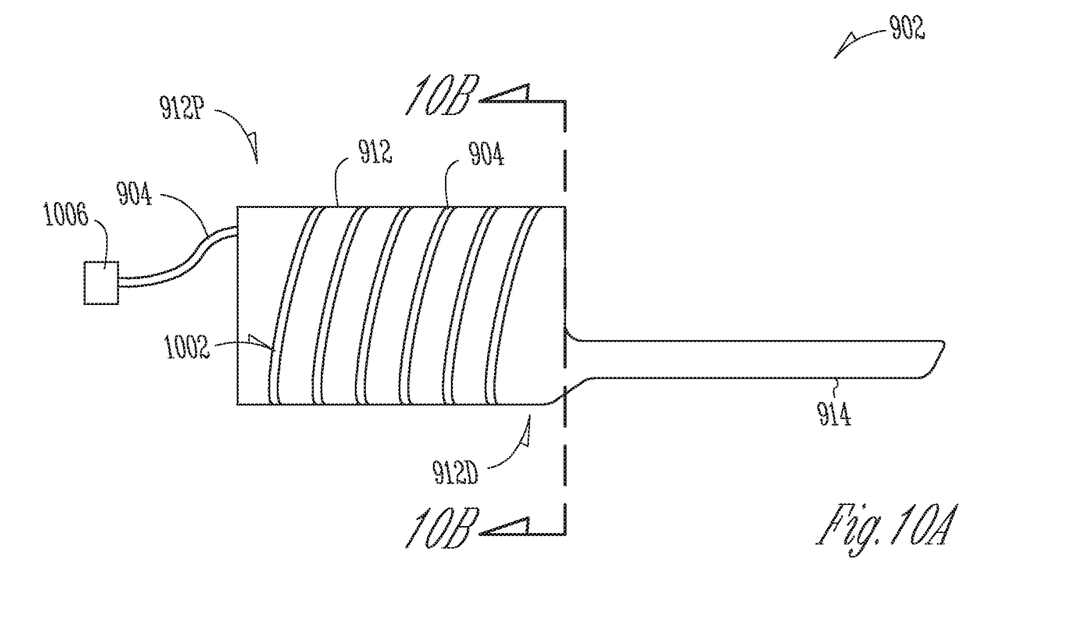
FIG. 10A is a side view of an FBG force sensor device in accordance with some embodiments.

FIG. 10A is a side view of the FBG force sensor device 902 in accordance with some embodiments. FIG. 108 is an illustrative cross-sectional view of the FBG force sensor of FIG. 10A taken along line 1-1. FIG. 11A is a top view of the FBG force sensor device 902 in accordance with some embodiments. FIG. 11B is an illustrative cross-sectional view of the FBG force sensor of FIG. 11A taken along line 2-2.

Referring to FIGS. 9A-9B, FIG. 10A and FIG. 11A, a first segment of the optical fiber 904 containing the first and second FBGs 906, 908 extends within the cap. A second segment of the optical fiber 904 extends in a helical path 1002 within the collar 912 between the proximal collar portion 912p and the distal collar portion 912d. A portion of the optical fiber 904 at the proximal collar 912p portion may couple to an external optical coupler 1006 for transmission of optical information to a signal processing device (not shown) to determine a tissue force, for example, sensed using based upon optical signals produced by the first and second FBGs 904, 906.

Figure 10B:
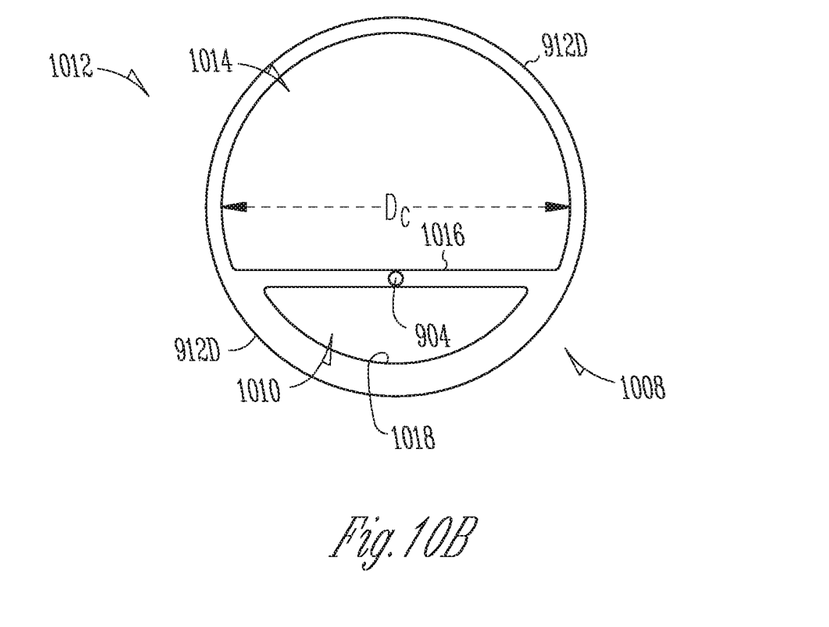
FIG. 10B is an illustrative cross-sectional view of the FBG force sensor of FIG. 10A taken along line 1-1.
Figure 11A:
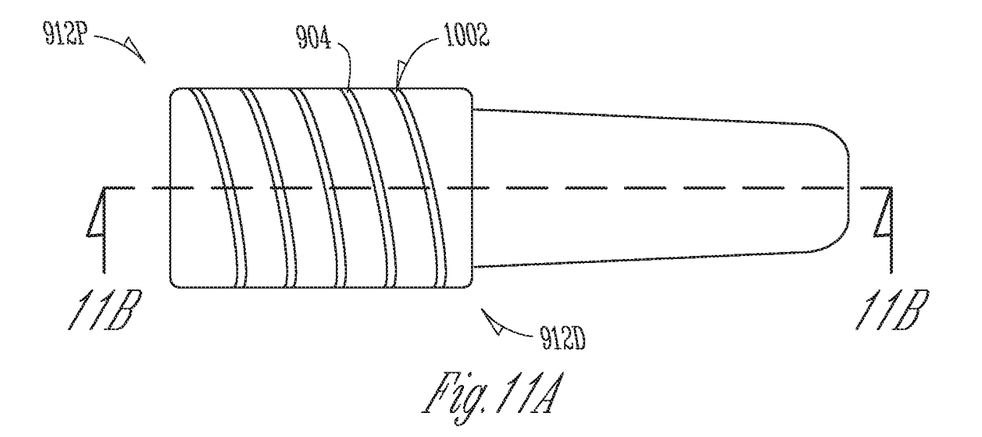
FIG. 11A is a top view of an FBG force sensor device in accordance with some embodiments.
Figure 11B:
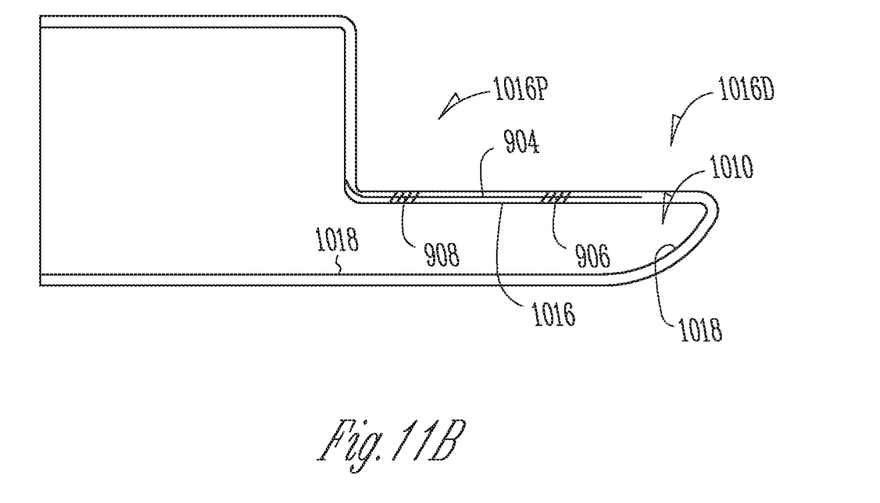
FIG. 11B is an illustrative cross-sectional view of the FBG force sensor of FIG. 11A taken along line 2-2.

Referring to the cross-sectional views of FIG. 10B and FIG. 11B, the collar 912 defines a flexible annular hollow tube that is sized to snugly fit about a 2-dof wrist 530 at a distal end 450 of a surgical instrument shaft 410. That is, the collar 912 fits about the 2-dof wrist 530 without slipping during normal use. More particularly, interior wall surface diameter ($D_C$) of the collar is sized to fit snugly against an external circumference of the 2-dof wrist 530 so as not to slip along the external surface during normal use. The cantilever cap 914 depends distally from a first portion 1008 of the distal collar portion 912d and defines a lumen 1010 that is sized to snugly fit about an end effector portion having a working surface at which a force may be sensed, such as a first jaw 504 of the end effector 502. That is, the cap 914 fits about the end effector portion 504 without slipping during normal use. More particularly, for example, interior wall contours of the cap 914 closely match external contours of the first end effector jaw 504. A second portion 1012 of the distal collar portion 912d defines a distal opening 1014 through which another end effector portion may extend, such as the second jaw 506 of the end effector 502. The cap 914 includes a first wall portion 1016 and a second wall portion 1018 that together define the lumen 1010. A segment of the optical fiber 904 in which the first and second FBGs 906, 908 are formed extends within the first wall portion 1016 of the cap 914. In some embodiments, the first FBGs 906 are embedded within a distal portion 1016d of the first wall portion 1016 that is configured to overlay a working surface 516 of the end effector 502 that may receive external tissues force and the second. FBGs 908 are embedded within a proximal portion 1016p of the first wall portion 1016 that overlays a non-working portion 520 of the end effector 502 that does not ordinarily receive external tissues force. Alternatively, the second FBGs 908 may be formed in a segment of the optical fiber 904 embedded within the collar 912. The first and second wall portions 1016, 1018 of the cap 914 are sized to snugly fit about an end effector having a working surface such as an first end effector jaw 504. The first wall portion 1016 is configured to overlay the end effector working surface 516 to position the first FBGs 906 embedded within the first wall portion 1016 to receive a tissue force imparted to the working surface 516, for example. The second wall portion 1018 is configured to overlay non-working surface portions of the end effector such as side and back surfaces of the first jaw 504.

Figure 12:
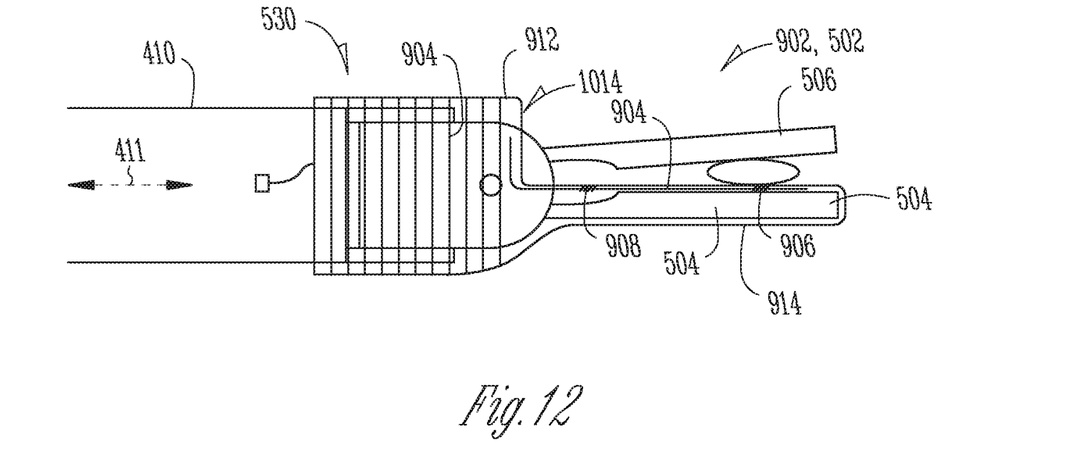
FIG. 12 is an illustrative partially transparent side view of the FBG force sensor device installed upon an end effector in accordance with some embodiments.

FIG. 12 is an illustrative partially transparent side view of the FBG force sensor device 902 installed upon the end effector 502 in accordance with some embodiments. The drawing is partially transparent to show the end effector 502 and 2-dof wrist 530 that are encompassed within the housing 910 of the FBG force sensor device 902. The end effector of FIG. 12 includes a pair of jaws 504, 506 at a distal end of a surgical instrument shaft 410 that currently are disposed in alignment with a central axis 411 of the shaft 410. The collar 912 is disposed about the 2-dof wrist 530 and a distal portion of the shaft 410. The cap 914 is disposed about the first jaw 504 of the end effector 502. The flexible material forming the housing 912, 914 may have a surface friction property that cause the collar 912 to grip the distal end the 2-dof wrist 530 and the distal end portion of the shaft 410 and that cause the cap 914 to grip the first jaw 504 so that the housing 912, 914 does not readily slide off during normal surgical use. A second jaw 506 of the end effector 502 extends through the opening 1014 at the distal collar portion 912d. The jaws are in a closed position with anatomical tissue captured between them. A tissue force $F_T$ exerted upon the working surface of the first jaw is imparted through the housing material at the first wall portion of the cap to the first FBGs disposed at a distal portion of the cap. In some embodiments, the housing material has a thickness of (WHAT?) to be thick enough to provide some protection against damage to the embedded first FBGs while being thin enough to reliably impart the tissue force $F_T$ to the embedded first FBGs. The second FBRs, which are not subject to the tissue force may be used for temperature calibration of the first FBGs. The helically wound segment of the optical fiber transmits optical information between the first and second FBGs and the external optical coupler.

Figure 13:
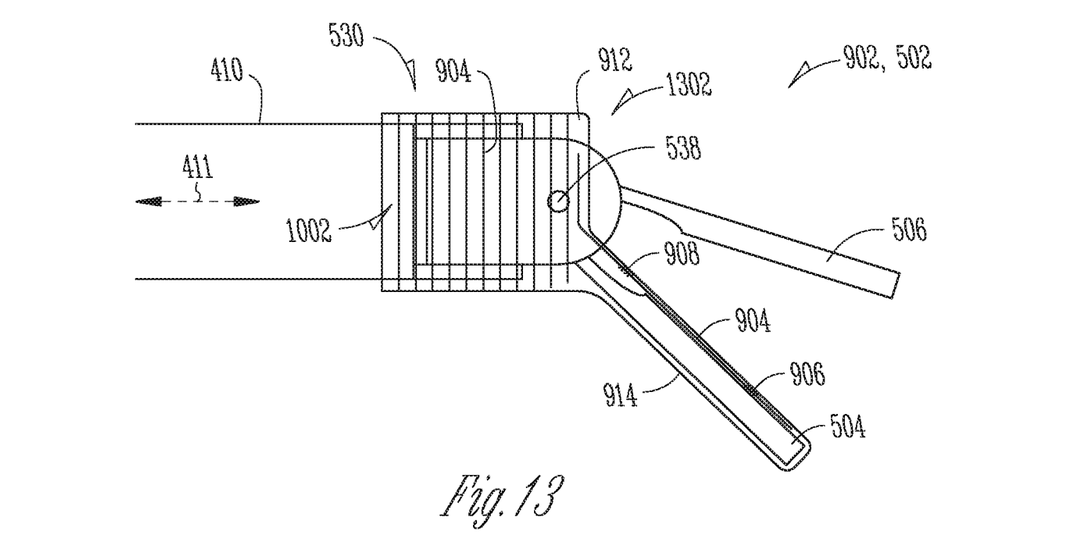
FIG. 13 is an illustrative partially transparent side view of the FBG force sensor device installed upon an end effector in accordance with some embodiments.

FIG. 13 is an illustrative partially transparent side view of the FBG force sensor device 902 installed upon an end effector 502 in accordance with some embodiments. The drawing is partially transparent to show the end effector 502 and 2-dof wrist 530 that are encompassed within the housing 912, 914 of the FBG force sensor device 902. The end effector 502 of FIG. 13 includes a pair of jaws 504, 506 in an open position and rotated about the distal pivot axis 538 to be non-aligned with the shaft, center axis 411. The pivoting of the end effector jaws 504, 506 to a position that is non-aligned with the shaft center axis 411 may result in distal direction strain and stretch of the housing material in certain regions of the housing 912, 914 such as the region indicated by reference numeral 1302. However, the helical winding pattern 1002 of the optical fiber 904 reduces the amount of this strain and stretch imparted to the optical fiber 904.

Figure 14:
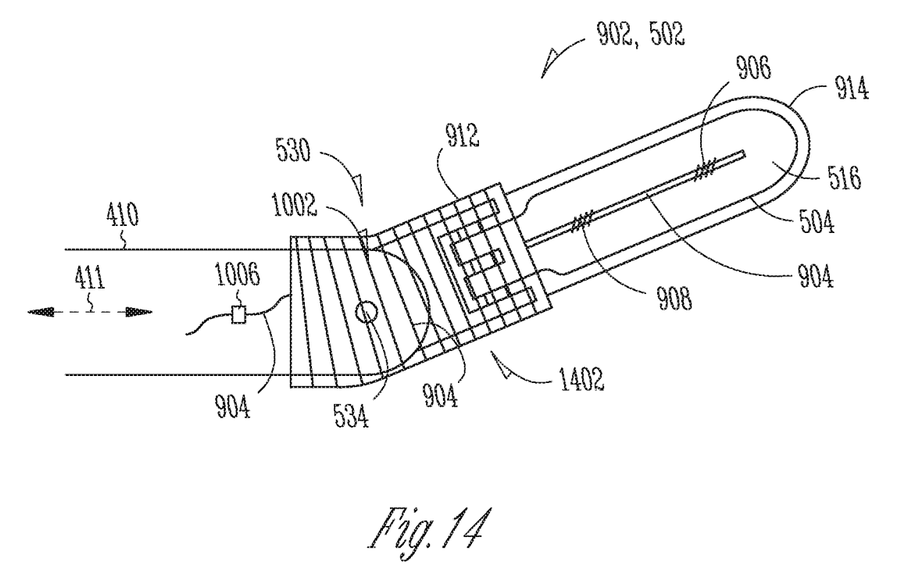
FIG. 14 is an illustrative partially transparent top view of the FBG force sensor device installed upon an end effector in accordance with some embodiments.

FIG. 14 is an illustrative partially transparent top view of the FBG force sensor device 902 installed upon an end effector 502 in accordance with some embodiments. The drawing is partially transparent to show the end effector 502 and 2-dof wrist 530 that are encompassed within the housing 912, 914 of the FBG force sensor device 902. The second jaw 506 also is transparent so as to show the first optical fiber segment 904 and the first and second. FBGs 906, 908 embedded within the first wall portion 1016 of the cap 914. The end effector jaws 504, 506 are rotated about the proximal pivot axis 534 to be non-aligned with the shaft center axis 411. The pivoting of the end effector jaws 504, 506 to a position that is non-aligned with the shaft center axis 411 may result in distal direction strain and stretch of the housing material in certain regions of the housing 912, 914 such as the region indicated reference numeral 1402. As explained above, however, the helical winding pattern 1002 of the optical fiber 904 reduces the amount of this strain and stretch imparted to the optical fiber 904.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the disclosure should be limited only by the following claims, and it is appropriate that the claims be construed broadly and in a manner consistent with the scope of the embodiments disclosed herein. The above description is presented to enable any person skilled in the art to create and use a wire rope with enhanced wire wrap. Various modifications to the embodiments will be readily apparent to those skilled in the art, and the generic principles defined herein may be applied to other embodiments and applications without departing from the scope of the invention. In the preceding description, numerous details are set forth for the purpose of explanation. However, one of ordinary skill in the art will realize that the invention might be practiced without the use of these specific details. In other instances, well-known processes are shown in block diagram form in order not to obscure the description of the invention with unnecessary detail. Identical reference numerals may be used to represent different views of the same or similar item in different drawings. Thus, the foregoing description and drawings of embodiments in accordance with the present invention are merely illustrative of the principles of the invention. Therefore, it will be understood that various modifications can be made to the embodiments by those skilled in the art without departing from the scope of the invention, which is defined in the appended claims.

What is claimed is:

1. A force sensing device for use with a surgical instrument including a shaft, a two degree-of-freedom wrist mounted to the shaft, and an end effector portion mounted to the wrist and including a working surface, the force sensing device comprising:
   a housing defining an annular collar sized to snugly fit about the two degree-of-freedom wrist and defining a cap sized to snugly fit about the end effector portion;
   an optical fiber including a first segment within the annular collar and including a second segment within the cap; and
   a first fiber Bragg grating (FBG) formed in the second segment of the optical fiber.

2. The force sensing device of claim 1, wherein;
   the first FBG is within a portion of the cap configured to overlay the working surface of the end effector portion.

3. The force sensing device of claim 1, wherein:
   the force sensing device further includes a second FBG formed in the second segment of the optical fiber; and
   the second FBG is within a portion of the cap configured to overlay a non-working surface of the end effector portion.

4. The force sensing device of claim 1, wherein:
   the first FBG is within a portion of the cap configured to overlay the working surface of the end effector portion;
   the force sensing device further includes a second FBG formed in the second segment of the optical fiber within a portion of the cap; and
   the second FBG is within a portion of the cap configured to overlay a non-working surface of the end effector portion.

5. The force sensing device of claim 1, wherein:
   the first optical fiber segment follows a helical path within the annular collar.

6. The force sensing device of claim 1, wherein:
   the cap depends from the annular collar and defines a lumen sized to snugly fit about the end effector portion.

7. The force sensing device of claim 1, wherein:
   the cap includes a first wall portion and a second wall portion, and the first and second wall portions together define a lumen sized to snugly fit about the end effector portion;

the first wall portion is configured to overlay the working surface of the end effector portion;
the second wall portion is configured to overlay a portion of the end effector portion facing away from the working surface of the end effector portion; and
the first FBG is within the first wall portion.

8. The force sensing device of claim 1, wherein:
the annular collar includes a proximal collar portion and a distal collar portion;
the cap depends from the distal collar portion and defines a lumen sized to snugly fit about the end effector portion; and
the first optical fiber segment follows a helical path within the annular collar between the proximal collar portion and the distal collar portion.

9. The force sensing device of claim 1, wherein:
the housing is formed of a flexible material.

10. A surgical instrument comprising:
an elongated shaft that includes a proximal end and a distal end;
a two-degrees-of-freedom wrist at the distal end of the shaft;
an end effector that includes first and second jaws mounted to the two-degrees-of-freedom wrist;
a removable housing formed of a flexible material and defining an annular collar snugly fit about the two-degrees-of-freedom wrist and a cap snugly fit about the first jaw;
an optical fiber including a first segment within the annular collar and a second segment within the cap; and
a first fiber Bragg grating (FBG) formed in the second segment of the optical fiber.

11. The surgical instrument of claim 10, wherein:
a distal opening is defined in the housing; and
the second jaw extends through the distal opening.

12. The surgical instrument of claim 10, wherein:
the first jaw includes a working surface; and
the first FBG is embedded in a portion of the cap overlaying the working surface of the first jaw.

13. The surgical instrument of claim 10, wherein:
the surgical instrument further includes a second FBG formed in the first segment of the optical fiber within the cap;
the first law includes a non-working surface; and
the second FBG is in a portion of the cap overlaying the non-working surface of the first jaw.

14. The surgical instrument of claim 10, wherein:
the surgical instrument further includes a second FBG formed in the second segment of the optical fiber;
the first law includes a working surface and a non-working surface;
the first FBG is within a portion of the cap overlaying the working surface of the first jaw; and
overlaying the non-working surface of the first jaw.

15. The surgical instrument of claim 10, wherein:
the first optical fiber segment follows a helical path within the annular collar.

16. The surgical instrument of claim 10, wherein;
the first jaw includes a working surface and a portion of the first jaw facing away from the working surface;
the cap includes a first wall portion and a second wall portion, and the first and second wall portions together define a lumen sized to snugly fit about the first jaw;
the first wall portion overlays the working surface of the first jaw;
the second wall portion overlays the portion of the first jaw facing away from the working surface; and
the first FBG is within the first wall portion.

\* \* \* \* \*

UNITED STATES PATENT AND TRADEMARK OFFICE
CERTIFICATE OF CORRECTION

PATENT NO. : 11,980,504 B2
APPLICATION NO. : 17/058630
DATED : May 14, 2024
INVENTOR(S) : John Ryan Steger It is certified that error appears in the above-identified patent and that said Letters Patent is hereby corrected as shown below:

In the Claims

Column 8, Line 39 (Claim 2): ". . . claim 1, wherein; . . ." should be -- claim 1, wherein: --

Column 8, Line 61 (Claim 6): ". . . the cap depends from . . ." should be -- the cap extends from --

Column 9, Line 10 (Claim 8): ". . . the cap depends from . . ." should be -- the cap extends from --

Column 10, Line 9 (Claim 13): ". . . the first law . . ." should be -- the first jaw --

Column 10, Line 16 (Claim 14): ". . . the first law . . ." should be -- the first jaw --

Column 10, Lines 19-20 (Claim 14): ". . . and overlaying the non-working surface of the first jaw." should be -- and the second FBG is in a portion of the cap overlaying the non-working surface of the first jaw --

Column 10, Line 24 (Claim 16): ". . . claim 10, wherein; . . ." should be -- claim 10, wherein: --

Signed and Sealed this
Twenty-fifth Day of June, 2024

Katherine Kelly Vidal
*Director of the United States Patent and Trademark Office*